United States Patent [19]

Komatsu et al.

[11] Patent Number: 5,426,251

[45] Date of Patent: Jun. 20, 1995

[54] PROCESS FOR PREPARING 1,1,1-TRIFLUORO-2-CHLOROETHANE AND/OR 1,1,1,2-TETRAFLUOROETHANE

[75] Inventors: Satoshi Komatsu; Satoshi Koyama; Yoshinori Tanaka; Takehide Tsuda, all of Osaka, Japan

[73] Assignee: DAIKIN Industries, Ltd., Osaka, Japan

[21] Appl. No.: 90,077

[22] PCT Filed: Nov. 27, 1992

[86] PCT No.: PCT/JP92/01552

§ 371 Date: Jul. 21, 1993

§ 102(e) Date: Jul. 21, 1993

[87] PCT Pub. No.: WO93/11093

PCT Pub. Date: Jun. 10, 1993

[30] Foreign Application Priority Data

Nov. 27, 1991 [JP] Japan ................... 3-312328

[51] Int. Cl.$^6$ ................. C07C 17/08; C07C 17/38
[52] U.S. Cl. ...................... 570/165; 570/178
[58] Field of Search ................... 570/178, 165

[56] References Cited

U.S. PATENT DOCUMENTS 3,558,438 1/1971 Schoenbeck ................. 570/178
4,944,846 7/1990 Manzer et al. ............... 570/178

FOREIGN PATENT DOCUMENTS

446869A1 3/1991 European Pat. Off. .
449614A2 3/1991 European Pat. Off. .
449617A2 3/1991 European Pat. Off. .
90/08755 8/1990 WIPO .

*Primary Examiner*—Alan Siegel
*Attorney, Agent, or Firm*—Birch, Stewart, Kolasch & Birch

[57] ABSTRACT

A process for preparing 1,1,1-trifluoro-2-chloroethane and/or 1,1,1,2-tetrafluoroethane, comprising the steps of reacting trichloroethylene and/or 1,1,1-trifluoro-2-chloroethane with hydrogen fluoride in the presence of a fluorinating catalyst in a gas pase, separating 1,1,1-trifluoro-2-chloroethane, hydrogen fluoride, and optionally trichloroethylene, from the reaction mixture obtained by the above reaction which contains 1,1,1-trifluoro-2-chloroethane, 1,1,1,2-tetrafluoroethane, hydrogen fluoride, and optionally trichloroethylene, and recycling them to the reaction step above, characterized in that at least a part of the reaction mixture is distilled in a distillation tower, 1,1,1,2-tetrafluoroethane-rich components are discharged from the top of the tower, and a mixture of 1,1,1-trifluoro-2-chloroethane and hydrogen fluoride, and optionally trichloroethylene, is discharged in the form of gas from the middle part of the tower at a temperature which is above the boiling point of the azeotropic mixture of 1,1,1-trifluoro-2-choroethane and hydrogen fluoride and at least 5° C. below the boiling point of anhydrous hydrogen fluoride under the internal pressure in the distillation tower and returned to the reaction step.

The discharging at the middle part of the tower provides a recycling gas in high purity, while leaving higher-boiling substances such as water, tar, etc. on the bottom of the tower. The gas can be used for the reaction system as a recycling gas, which can eliminate a process of vaporizing high-boiling mixture which is conventionally discharged at the bottom of the tower by means of a vaporizer and the like and reduce the equipment cost significantly.

5 Claims, No Drawings

PROCESS FOR PREPARING 1,1,1-TRIFLUORO-2-CHLOROETHANE AND/OR 1,1,1,2-TETRAFLUOROETHANE

FIELD OF THE INVENTION

The present invention relates to a process for preparing 1,1,1-trifluoro-2-chloroethane (referred to as R-133a hereinafter) and/or 1,1,1,2-tetrafluoroethane (referred to as R-134a hereinafter), which comprises reacting trichloroethylene and/or R-133a with hydrogen fluoride (referred to as HF hereinafter) in the presence of a fluorinating catalyst, and separating R-133a, HF, and optionally trichloroethylene, from the reaction mixture, and recycling them to the reaction process.

R-133a is useful as an intermediate of fluorinated organic compounds. R-134a is used as a coolant and a blowing agent as a substitute for dichlorodifluoroethane which is one of the recently regulated halocarbons.

DESCRIPTION OF THE PRIOR ART

R-133a and R-134a are usually produced by fluorinating trichloroethylene with HF in a gas phase in the presence of a catalyst which comprises chromium. R-134a is also produced from R-133a and HF by a similar way to the above method. These reactions proceed stepwise and are shown by the following scheme:

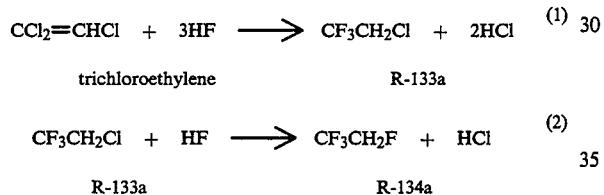

There is a reverse reaction of from the right side to the left side in the reaction (2) which provides R-134a. Moreover, it proceeds about 100 times as fast as the reaction of from the left to the right. Therefore, HF must be used in large excess even in a relatively efficient gas phase reaction. However, it is difficult to obtain R-133a in a conversion of more than 30%. Accordingly, it is necessary to separate unreacted R-133a and HF from the reaction mixture and to recycle them to the reaction process. However, the prior arts only describe a method in which the whole reaction mixture is washed with water. There has been known no method in which the unreacted R-133a and HF can be efficiently separated and recycled.

The reaction mixture obtained in the process comprising the gas phase reaction contains R-133a, R-134a, hydrogen chloride, HF, and optionally trichloroethylene. When trichlroethylene is completely fluorinated in the reaction process, or when R-133a is fluorinated, substantially no trichloroethlene is contained in the reaction mixture. However, even in those cases, the reaction mixture is seldom completely free from trichloroethylene and usually contains as much as 0.1 mole % trichloroethylene. In addition, the mixture inevitably contains a small amount of water which is present in the starting materials. Water, even in a small amount, lowers the activity of the catalyst used and prevents the reaction.

In a usual way, the reaction mixture which has been cooled is charged to a distillation tower. The low-boiling mixture consisting of hydrogen chloride which shifts the equlibrium of the reaction (2) to the left side and an azeotropic mixture of R-134a and HF is discharged from the top of the distillation tower, and the high-boiling mixture, consisting predominantly of R-133a and HF, and optionally trichloroethylene, is discharged from the bottom of the tower. Thereafter, the high-boiling mixture is vaporized with a vaporizer and recovered as a recycling gas in the reaction system. In this method, a vaporiser is required in addition to the distillation tower, which makes equipment very complicated. Moreover, in this method, the small amount of water which is contained in the reaction mixture is also recyled to reaction step and accumulated in the reaction system. Thus the method in which R-133a and HF are separated from the reaction mixture and recycled to the reaction step has the problems that impurities are incorporated into reaction system, and that a great deal of equipment to provide heat is required.

SUMMARY OF THE INVENTION

The inventors have made intense studies to solve the above problems and found the following facts: R-133a and HF, and trichloroethylene and HF form azeotropic compositions respectively, which, moreover, are minimum boiling mixtures, different from the azeotropic composition of water and HF; under a certain pressure, a mixture of any composition consisting of HF, R-133a and trichloroethylene has an equilibrium temperature between the boiling point of the azeotropic composition of R-133a and HF and the boiling point of HF; since the temperature is remote from the azeotropic point of water and HF, a mixture of the above three compounds can be easily obtained in a high purity. The inventors have further found that, when the reaction mixture of the fluorination is distilled to separate the components, a gaseous mixture which has been separated and discharged from the middle part of the distillation tower can be recycled to the reaction step, which enables the omission of vaporizing facilities usually required.

Accordingly, the present invention provides a process for preparing R-133a and/or R-134a, comprising the steps of reacting trichloroethylene and/or R-133a with hydrogen fluoride in the presence of a fluorinating catalyst in a gas phase, separating R-133a, hydrogen fluoride, and optionally trichloroethylene, from the reaction mixture containing R-133a, R-134a, hydrogen fluoride, and optionally trichloroethylene, which are obtained by the above reaction, and recycling R-133a, hydrogen fluoride, and optionally trichloroethylene to the reaction step, characterized in that at least a part of the reaction mixture is distilled in a distillation tower, R-134a-rich components are discharged from the top of the tower, and that a mixture of R-133a, hydrogen fluoride, and optionally trichloroethylene, is discharged in the form of gas from the middle part of the tower at a temperature which is above the boiling point of the azeotropic mixture of R-133a and hydrogen fluoride and at least 5° C. below the boiling point of anhydrous hydrogen fluoride under the internal pressure in the distillation tower and returned to the reaction step.

DETAILED DESCRIPTION OF THE INVENTION

The process according to the present invention can be applied to any composition used in the reaction of trichloroethylene, R-133a or both of them with HF in a gas phase.

The reaction mixture obtained by the reaction process is a gas containing mainly R-133a, R-134a, hydrogen chloride and HF, and occasionally trichloroethylene. They are cooled usually to a temperature of from −50° C. to 50° C. and most of them are liquefied and charged to a distillation tower. However, a method for charging the reaction mixture to the distillation tower is not limited to the one mentioned above. In addition to liquid charging, the gas which can not be liquefied may be charged to the distillation tower under an elevated pressure, if necessary, or the whole mixture may be charged thereto without liquefication under an elevated pressure. In addition, the reaction mixture may be charged thereto in the form of a liquid, a gas or a mixed phase under the inherent pressure of the mixture.

The pressure in the distillation tower is not particularly limited, but is usually from atomospheric pressure to 20 atm. If the pressure is lower than atomspheric pressure, a considerable amount of energy is required for cooling at the top of the tower. When the pressure exceeds 20 atm., the expense for a pressure-proof distillation tower is needed.

The reaction mixture introduced into the distillation tower is separated into a low-boiling mixture containing mainly hydrogen chloride, R-134a and HF, and a high-boiling mixture containing mainly R-133a, trichloroethylene and HF. The low-boiling mixture is discharged from the top of the tower and the high-boiling mixture is discharged from a middle part of the tower which is positioned below the charging part of the reaction mixture and above the bottom of the tower. The discharging temperature should be above the azeotropic point of R-133a and HF, and at least 5° C. below the boiling point of HF. Otherwise, R-134a, water, etc. are circulated in the reaction process. The azeotropic points of R-133a and HF are 20° C. and 66° C. under pressures of 5 kg/cm$^2$G and 9 kg/cm$^2$G, respectively. The boiling points of HF are 47° C. and 102° C. under pressures of 5 kg/cm$^2$G and 9 kg/cm$^2$G, respectively. Trichloroethylene has a boiling point of 120° C. under a pressure of 1.5 kg/cm$^2$G and therefore, in usual cases, remains on the bottom of the tower as the high boiling substance. However, since the azeotropic point of trichloroethylene and HF is 41° C. under a presure of 1.5 kg/cm$^2$G, it can be discharged in the above temperature range.

Discharge of the high-boiling mixture from the middle part of the distillation tower provides a recycling gas of high purity, with remaining higher-boiling substances such as water, tar, etc. on the bottom of the distillation tower. The recycling gas as such can be used for the reaction system. Thus it is possible to eliminate the convetional procedure of vaporizing the high-boiling mixture which has been discharged from the bottom of the distillation tower with a vaporizer. The simplification of facilities reduces the cost of facilities.

Water, tar, etc. which are dischgarged from the bottom of the tower usually contain HF. They may be distilled in a separate distillation tower in order to recover HF which is a useful substance.

The ratio of R-133a and HF, which are discharged from the middle part of the tower, has a great influence on the fluorinating reaction. Therefore, it can be suitably adjusted by adding HF to the distillation tower.

When R-133a is intended to be obtained alone, it can be discharged as a constant boiling mixture of R-133a and HF at an upper part of the tower above the part for discharging the recycling gas.

EXAMPLES

Example 1

In a distillation column (the number of thoretical plates: 35, a column diameter: 50 mm) having a 5 l vessel below it and a condenser above it, there were charged 2 moles of R-134a, 25 moles of R-133a and 70 moles of HF, and a refluxed condition was made in such a manner that a pressure of 9 kg/cm$^2$G was kept without discharging any component. At this time, the temperature at the top of the column was 39° C. The refluxing liquid had a composition of 95 mole % of R-134a and 5 mole % of HF, which was an azeotropic composition of R-134a and HF. A gaseous reaction mixture of the reaction of R-133a with HF and/or trichloroethylene with HF was cooled to 0° C. Only the resulting liquid phase was introduced in the distillation column with a pump. The flow rates are shown in Table 1.

TABLE 1

| Component | Gaseous Reaction Mixture | | Liquid charged to Column | |
| --- | --- | --- | --- | --- |
| | Flow rate (mol/hr) | Composition (mole %) | Flow rate (mol/hr) | Composition (mole %) |
| R-133a | 87 | 19.9 | 84 | 22.0 |
| R-134a | 14 | 3.2 | 8 | 2.1 |
| HF | 294 | 67.3 | 288 | 75.4 |
| HCl | 42 | 9.6 | 2 | 0.5 |
| Trichloroethylene | 0.1 | (0.02) | 0.1 | (0.03) |
| Water | 0.01 | 20 ppm | 0.01 | 30 ppm |
| Others | 0.1 | (0.02) | 0.1 | (0.03) |

Since the pressure increased as the liquid was introduced, it was kept at 9 kg/cm$^2$G by discharging a gas thorough the outlet of the condenser. An uncondesed gas was washed with water, dried, and liquified under an elevated pressure to store it in a container. After about 5 minutes, since the gas temperature in the neighborhood of the discharging outlet at the third plate from the bottom of the column became 90° C., discharging was started with keeping the volume of the liquid in the vessel constant. The discharged gas as such was returned to the reactor only with the addition of HF and trichloroethylene consumed. This procedure was continued. After 2 hours, an analysis was made for the compositions of the recycling gas, the discharged gas at the top of the colomn and the liquid in the vessel. At this time, the discharging temperature was 88° C.

The content of acidic components, i.e. HF and hydrogen chloride, was determined as follows: At first, a sample was absorbed into water to make an aqueous solution. The total content of acidic components was determined by titrating the aqueous solution. On the other hand, the ratio of chloride ion to fluoride ion was determined by ion chromatography. The individual contents of the acidic components were calculated from the values determined above. Organic substances were analyzed by gas chromatography after washing with water and drying. The water content was determined by the Karl-Fisher method. The compositions are given in Table 2. Table 2 shows that water can be removed efficiently, and the useful unreacted substances which had been introduced into the distillation tower, i,e. HF, R-133a and trichloroethylene, can be recovered without any loss, and that they are of high purity.

Comparative Example 1

Example 1 was repeated except that the discharging was started when the temperature of the discharging outlet became 65° C. The composition of the discharged gas are given in Table 2, which shows that the gas is contaminated with R-134a.

Example 2 and Comparative Example 2

Example 1 was further continued. After 12 hours, the temperature of the dischaging outlet began to rise gradually. The compositions of the discharged gases obtained when the temperatures of the discharging outlet were 95° C. and 100° C., were shown at the columns of Example 2 (95° C.) and Comparative Example 2 (100° C.) in Table 2, respectively.

TABLE 2

| Component | Composition (mole %) | | | |
|---|---|---|---|---|
| | Example 1 | Com. Exam. 1 | Example 2 | Com. Exam. 2 |
| R-133a | 20 | 30 | 10 | 5 |
| R-134a | trace | 1 | trace | trace |
| HF | 80 | 69 | 90 | 95 |
| HCl | N/D | N/D | N/D | N/D |
| Trichloroethylene | (0.03) | trace | (0.03) | (0.03) |
| Water | trace | trace | trace | 25 ppm |
| Others | trace | trace | trace | trace |

Example 3

Example 1 was repeated except that the discharging was effected at the vessel below the bottom of the tower in such a manner that a liquid volume in it was kept constant, instead of discharging at the third plate from the botom of the tower. Water was contained in an amount of 30 p.p.m. in the discharged liquid.

Effect of the Invention

As can be understood from the description above, according to the present invention, when the reaction mixture of the fluorinating reaction is cooled and charged in a distillation tower, a mixture of R-133a, trichloroethylene and HF containing no other impurity can be obtained at the middle of the lower part in the tower. In addition, the discharged mixture can be recycled directly to the reaction process by only heating it without a vaporizer, which enables the omission of a group of vaporizing facilities and the simplification of equipment. Moreover, it is possible to concentrate water and tar on the bottom of the distillation tower and easily remove them from the reaction-recycle system.

What is claimed is:

1. A process for preparing 1,1,1-trifluoro-2-chloroethane and/or 1,1,1,2-tetrafluoroethane, comprising the steps of:
    (a) reacting trichloroethylene and/or 1,1,1-trifluoro-2-chloroethane with hydrogen fluoride in the presence of a fluorinating catalyst in a gas phase;
    (b) separating a recycling mixture of 1,1,1-trifluoro-2-chloroethane, hydrogen fluoride, and optionally trichloroethylene, from the reaction mixture, which contains 1,1,1-trifluoro-2-chloroethane, 1,1,1,2-tetrafluoroethane, hydrogen fluoride, and optionally trichloroethylene; and
    (c) recycling the mixture separated in step (b) to the reaction process wherein at least a part of the reaction mixture is distilled in a distillation tower, 1,1,1,2-tetrafluoroethane-rich components are discharged from the top of the tower, and that said recycling mixture of 1,1,1-trifluoro-2-chloroethane, hydrogen fluoride, and optionally trichloroethylene, is discharged in the form of gas from the middle part of the tower at a temperature which is above the boiling point of the azeotropic mixture of 1,1,1-trifluoro-2-choroethane and hydrogen fluoride and at least 5° C. below the boiling point of anhydrous hydrogen fluoride under the internal pressure in the distillation tower and returned to the reaction step (a).

2. A process as claimed in claim 1, wherein the pressure in the distillaation tower is from atmospheric pressure to 20 atm.

3. A process as claimed in claim 1, wherein a mixture of hydrogen fluoride and water is discharged as liquid from the bottom of the distillation tower.

4. A process as claimed in claim 1, which further comprises adjusting a ratio of 1,1,1-trifluoro-2-chloroethane to hydrogen fluoride to be returned to the reaction process by adding hydrogen fluoride to the distillation tower.

5. A process as claimed in claim 1, wherein 1,1,1-trifluoro-2-chloroethane is discharged as an azeotropic mixture of 1,1,1-trifluoro-2-chloroethane and hydrogen fluoride at an upper part of the distillation tower above the part at which the 1,1,1-trifluoro-2-chloroethane and hydrogen fluoride recycling gas of step (b) is discharged.

* * * * *